United States Patent [19]

Banquy

[11] Patent Number: 4,782,096
[45] Date of Patent: Nov. 1, 1988

[54] PROCESS FOR THE PRODUCTION OF SYNTHESIS GAS

[75] Inventor: David Banquy, Paris, France

[73] Assignee: Foster Wheeler USA Corporation, Clinton, N.J.

[21] Appl. No.: 97,387

[22] Filed: Sep. 16, 1987

[51] Int. Cl.$^4$ .................. C07C 27/06; C07C 31/04
[52] U.S. Cl. ................................ 518/704; 518/713
[58] Field of Search ............................. 518/704, 713

[56] References Cited

U.S. PATENT DOCUMENTS 4,181,675  1/1980  Makin et al. .

FOREIGN PATENT DOCUMENTS 1262479  2/1972  United Kingdom .
1569014  1/1980  United Kingdom .

Primary Examiner—Howard T. Mars
Attorney, Agent, or Firm—Marvin A. Naigur; Lawrence M. Lavin

[57] ABSTRACT

A process for producing an organic compound from a hydrocarbon containing feedstock. The feedstock is divided into two fractions. The first is subject to a primary steam reforming reaction. The reaction product is then combined with the second fraction and reacted with a free oxygen-rich gas in a secondary reforming reactor to form a synthesis gas having a ratio of $$H_2/[2(CO)+3(CO_2)]$$

between 0.80 and 1.00. The synthesis gas is then mixed with a hydrogen-rich stream, which has been separated from a purge gas from the synthesis loop, to form a final synthesis gas. The final synthesis gas is injected into a synthesis loop in which the desired organic compound is formed. The purge gas extracted from the loop is subjected to a physical separation to form a hydrogen-rich gas stream and a residual gas stream. A portion of the hydrogen-rich stream is recycled to form the final synthesis gas.

15 Claims, 5 Drawing Sheets

PROCESS FOR THE PRODUCTION OF SYNTHESIS GAS

This application is a continuation, of application Ser. No. 827,558, filed Feb. 10, 1986.

BACKGROUND OF THE INVENTION

1. Field of the Invention

The present invention relates to a process for the production of organic compounds from a synthesis gas containing hydrogen and carbon oxides. The organic compounds prepared by this process may be a hydrocarbon, a mixture of hydrocarbons, an oxygenated compound (such as an alcohol, an ether, an ester, an acid, an anhydride, a ketone), or any mixture thereof. The invention is particularly useful for the production of methanol.

2. Description of the Prior Art

Processes for the preparation of various organic compounds from a synthesis gas containing hydrogen and carbon oxides are described in many prior patents and publications. By way of example: U.S. Pat. Nos. 2,829,313, 3,962,300, and 4,464,483, describe processes of the production of methanol; U.S. Pat. Nos. 4,413,064 and 4,088,671 describe processes of the production of hydrocarbons; M. J. Van der Burgt and S. T. Sie in a paper presented at the PETRO PACIFIC symposium at Melbourne, Australia, 16-19 September 1984 describe processes for the production of liquid hydrocarbons; and Ph. Courty et al "$C_1$-$C_6$ Alcohols from syngas" in Hydrocarbon Processing at page 105 (November 1984) describe the production of alcohols.

In these prior art processes, the organic compound is formed in a closed synthesis loop which includes the reactor in which the compound is formed and associated heat exchangers which permit separation of the desired product and recycle of the unreacted gases. Fresh synthesis gas is injected into the loop where it is combined with the recirculating gases. The mixture of fresh synthesis gas and recirculating gases are then fed to the reactor. The effluent from reactor containing the desired organic product is introduced into a heat exchanger wherein it is cooled to a sufficiently low temperature to cause the organic product to condense. The condensed product is withdrawn from the loop. Gases that are not condensed are recycled back to the reactor. However, a portion of these recycled gases is continuously purged from the loop in order to maintain the concentration of inerts, such as methane, argon, and nitrogen, at a reasonable level.

Although the present invention can be used for the production of numerous organic compounds, the remainder of this specification will focus on methanol since it is a large tonnage industrial product. Methanol is synthesized commercially by reforming a synthesis gas containing hydrogen, carbon monoxide, carbon dioxide, and small amounts of inert gases such as methane and nitrogen. The carbon oxides react with hydrogen to form methanol according to the following equations:

$$CO + 2H_2 \rightarrow CH_3OH$$

$$CO_2 + 3H_2 \rightarrow CH_3OH + H_2O$$

The synthesis gas is conveniently characterized by the following ratio of hydrogen to carbon oxides:

$$Z = \frac{\text{moles } H_2}{2(\text{moles CO}) + 3(\text{moles } CO_2)}$$

This synthesis gas composition is stoichiometric when $Z = 1.00$. In the production of higher alcohols from synthesis gas, the optimum synthesis gas composition is also very close to $Z = 1.00$, as reflected by the following general equations:

$$nCO + (2n)H_2 \rightarrow CH_3(CH_2)_{(n-1)}OH + (n-1)H_2O$$

$$nCO_2 + (3n)H_2 \rightarrow CH_3(CH_2)_{(n-1)}OH + (2n-1)H_2O$$

The Z ratio of hydrogen to carbon oxides is not universally used. By way of example, in U.S. Pat. No. 4,413,064, $CO_2$ is not considered as an active component in the reaction and the hydrogen to carbon oxides mole ratio is described in terms of $H_2/CO$. The preferred $H_2/CO$ mole ratio described in that patent is between 1.5 and 2.0. If $CO_2$ is included in the ratio, the optimum synthesis gas composition would actually correspond to a Z ratio appreciably lower than 1.00. Thus, when comparing the ratios of hydrogen to carbon oxides used in different processes, it is necessary to determine which carbon oxides are included in the ratio.

The optimum synthesis gas composition is the one that permits the use of the lowest pressure in the methanol synthesis loop for a given production rate, everything else being equal. This optimum composition may be identical to the stoichiometric composition (where $Z = 1.00$). However, because (1) of kinetic reasons connected to the activity and selectivity of the synthesis catalyst and (2) of differences in solubilities of the various reacting gases in liquid methanol, the optimum ratio may be slightly different from stoichiometric.

In the conventional process for producing methanol from a light hydrocarbon feedstock, ranging from natural gas to naphtha, a desulfurized feedstock is steam reformed at moderate pressure, in the range of 15 to 25 atm, and a high temperature, in the range of 850° to 900° C. The reforming reaction is endothermic and occurs in a reactor comprising refractory tubes externally heated by a set of burners, and filled with a fixed bed of catalyst made essentially of nickel on a refractory support. The synthesis gas is then cooled and compressed to the pressure used for the methanol synthesis, which ranges from 50 to 100 atm in the so-called "low pressure" processes, and which may reach 300 atm in the older high pressure processes. The pressurized gas is then introduced into the synthesis loop.

Because of the low carbon/hydrogen ratio of the light hydrocarbon feedstocks and the minimum steam rate which must be used in steam reforming, the synthesis gas produced has a composition very different from the stoichiometric composition required for methanol syhthesis. As a result, the synthesis loop operates with a very large excess of hydrogen. In addition to the non-stoichiometric synthesis gas composition, these prior art processes have a number of disadvantages which are particularly significant if a large capacity plant, i.e., one producing in excess of 2000 metric tons/day, is being used.

Because of the presence of excess hydrogen, the rate at which gases are purged from the loop must be very high. This results in a loop capacity that is appreciably lower than could be achieved if the synthesis gas had the stoichiometric composition. Furthermore, the reforming of the feedstock occurs at a low pressure. When the low-pressure is coupled with the high purge rate from the synthesis loop, it results in a poor overall efficiency.

Another disadvantage of these prior art processes is the excess $CO_2$ in the synthesis gas. Since the synthesis gas contains excess hydrogen and carbon dioxide, larger amounts of gases must be pressurized than would be necessary if the composition was stoichiometric. Because of the large quantity of synthesis gas that must be compressed, the horsepower and the dimensions of the synthesis gas compressor become excessive for methanol capacities above 2000 tons/day. The high $CO_2$ content creates another problem. It results in the formation of significant amounts of water in the synthesis loop, thereby increasing the cost of fractioning the methanol-water mixture that is condensed in the synthesis loop.

Finally, the cost of the steam reforming heater, which is a very large fraction of the overall plant cost, increases approximately linearly with capacity. This means that very little gain can be achieved by scaling up to a large single train capacity.

In place of the above-described conventional steam reforming process, a so-called "combination process" could be used. In this process the whole feedstock undergoes first a primary steam reforming reaction and then a secondary reforming with oxygen, in a single stage reactor operating adiabatically and packed with a single catalyst bed. Such a process, as described in U.S. Pat. No. 3,388,074, is widely used in the ammonia industry in which air is replaced by oxygen. Although this combination process allows the use of higher operating pressures in the synthesis gas generation, it does not easily achieve a final synthesis gas having the optimum composition required for methanol synthesis due to the minimum amount of steam that must be used in the primary steam reforming reaction. For the same reason, it does not permit the formation of a synthesis gas having a low $CO_2$ content. Furthermore, the large size of the primary steam reformer requires a high investment cost.

In U.S. Pat. No. 3,278,452, a process is described for the production of hydrogen and synthesis gases, in which part of the feedstock undergoes a primary steam reforming reaction, the effluent is mixed with the other fraction of the feedstock, and the mixture obtained is passed, in a secondary reforming reactor, through a succession of conversion zones with oxygen introduced between each until the desired conversion is reached. While this process, which is essentially oriented toward the production of hydrogen and ammonia synthesis gas, may to some extent yield a gas approaching the stoichiometric composition required for methanol synthesis, it still leads to a high $CO_2$ content in the synthesis gas and it requires a costly multistage reactor to perform the oxygen reforming reaction. Furthermore, the injection of oxygen between the successive catalyst beds, operating at very high temperatures, requires the solution of very elaborate technological problems. A multistage oxygen reforming reactor is required in this process because of the high concentration of hydrocarbons in the feed to the secondary reformer. If all the oxygen was introduced in a single stage reaction, carbon formation wold result and excessive temperatures would be required in the secondary reformer.

Furthermore, it has been reported in the prior art, as outlined in U.S. Pat. No. 3,278,452, that in a single stage secondary oxygen reforming of a hydrocarboncontaining feedstock, the maximum amount of conversion that may be achieved is such that the percentage methane equivalent of the product gas is about one-fifth of that of the feedstock, when the latter is above 25 percent. The expression "percent methane equivalent" as used herein means mole percent of hydrocarbons expressed as methane on a dry basis, e.g., ten mole percent ethane is 20 percent methane equivalent.

In British Patent No. 1,569,014, a process is described for the production of a synthesis gas having essentially the stoichiometric composition for methanol synthesis, that is with a Z ratio very close to or equal 1.00. In this process, a fraction of the feedstock is steam reformed in a primary steam reformer after which it is combined with another fraction of the feedstock, and the mixture is reacted with oxygen in a single stage secondary reformer operating under essentially adiabatic conditions. This process has the advantage of avoiding all the drawbacks mentioned above for the conventional processes, and in particular of reducing the investment cost, mostly due to an appreciable reduction of the size of the steam reforming heater. However, in order to achieve a near stoichiometric composition on the final synthesis gas, there is a limitation to such a reduction of the steam reformer size in the process. This is so because, in the primary steam reformer, the amount of hydrogen produced is much more than the soichiometric amount corresponding to the carbon oxides produced, whereas in the secondary oxygen reformer more hydrogen is burned than carbon monoxide. In other words, the primary steam reformer leads to a high Z ratio, whereas the secondary oxygen reformer reduces the Z ratio of the synthesis gas. Therefore, a balance should be maintained between the primary and secondary reformers in order to reach a stoichiometric composition at the outlet of the secondary reformer.

In the process of the present invention, which also combines a primary steam reformer with a secondary oxygen reformer, there is no need to maintain a balance between the primary and secondary reformers, because the synthesis gas composition at the outlet of the secondary reformer deviates purposely from the stoichiometric composition, with a Z ratio appreciably lower than 1.00, and, therefore, much less reforming is performed in the primary reformer, which reduces appreciably the cost of the overall plant.

SUMMARY OF THE INVENTION

The main object of the present invention is to reduce further the investmest cost of a methanol (or organic compound) plant, by reducing further the size of the steam reforming heater.

Another object of the present invention is to reduce the size and the weight of the overall methanol plant, thereby aking it easier to build on a large scale as a single stream plant, or to build on a ship or a barge.

In the process of the present invention, the steam reforming reaction and the oxygen reforming reaction are combined in a way which allows the operation at high pressure, in a similar way as described in British Patent No. 1,569,014 by operating the steam reforming at a much lower temperature than conventional processes. It also permits the use of an overall steam rate per unit of total feedstock that is lower than is possible with plain steam reforming, by treating in the primary steam reforming only a fraction of the total feedstock, but usually a lower fraction than in the process of British Patent No. 1,569,014, thereby producing a raw synthesis gas at the outlet of the secondary oxygen reformer with a Z ratio between 0.8 and 1.00.

The raw synthesis gas thus produced is mixed with a hydrogen-rich stream extracted from the purge gas of the synthesis loop, thereby increasing the Z ratio, and the mixture is injected into the synthesis loop where the desired organic compound is produced. The purge gas from the synthesis loop is subjected to a physical separation producing on one hand a hydrogen rich gas which is recycled as mentioned above, and on the other hand a residual gas which can be used as fuel in the primary steam reformer.

DESCRIPTION OF THE PREFERRED EMBODIMENTS

Any feedstock which can undergo a steam reforming reaction can be used as a feedstock in the process of the present invention. These feedstocks are light hydrocarbons ranging from methane to a naphtha having an end point of about 220° C.

It is well known that all the catalytic processes, whether steam or oxygen reforming, for the production of synthesis gases from a hydrocarbon feedstock, require that the feedstock be thoroughly desulfurized prior to the synthesis gas generation step. Therefore, the feedstock should be desulfurized before it is introduced into the steam or oxygen reformer.

Figure 1:
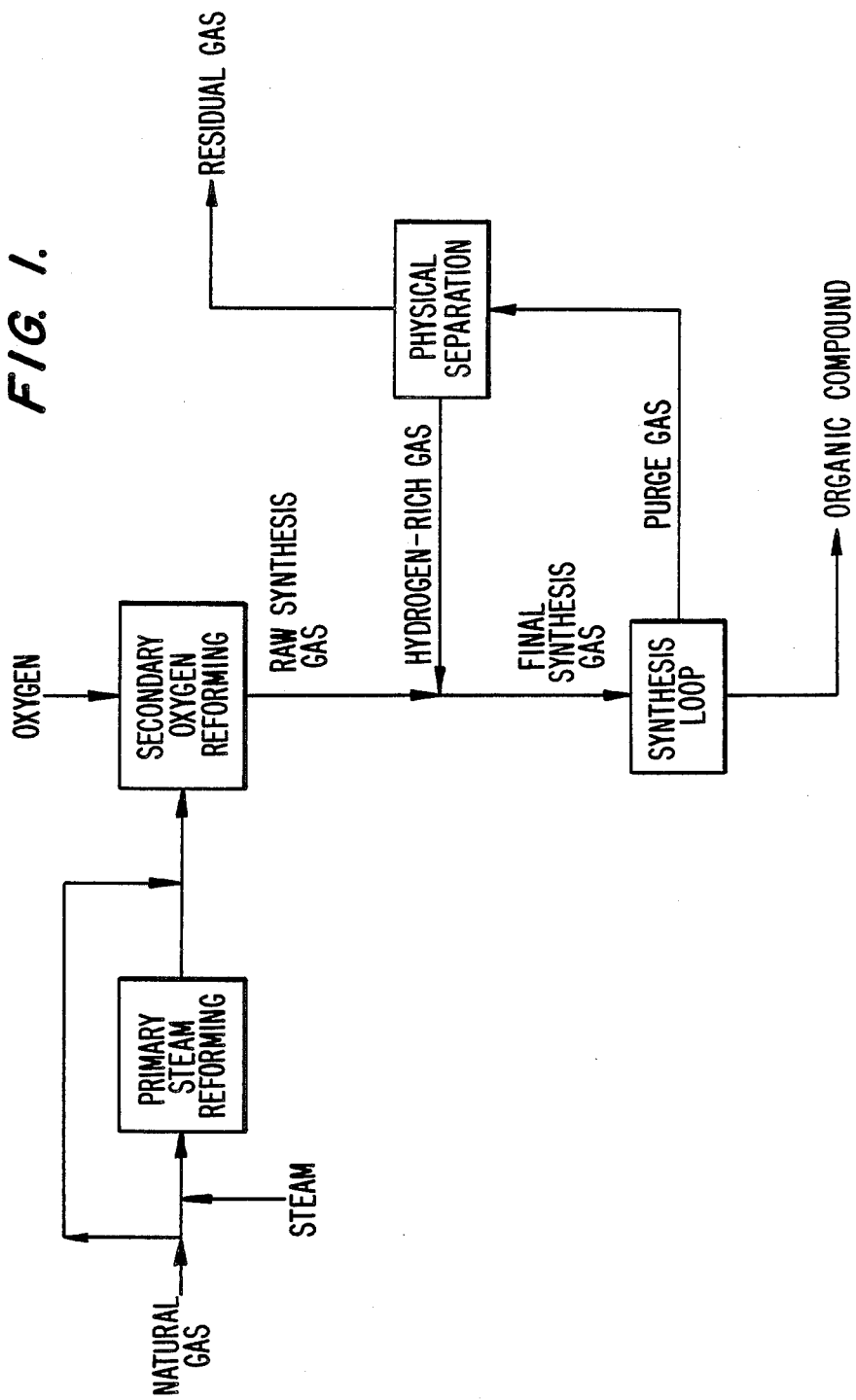
FIG. 1 is a block flow diagram of the basic process steps of the invention.

As shown in FIG. 1, the present invention is primarily concerned with a process for producing an organic compound in which a hydrocarbon-containing feedstock is first split into two feedstock fractions or streams, one fraction is subjected to a primary steam reforming, the resulting gaseous effluent is combined with the second feedstock fraction to form a mixture, and the mixture is then reacted with an oxygen containing gas in a secondary reforming reactor. The raw synthesis gas thus produced has a Z ratio which is purposely below the optimum desired for the synthesis loop, and comprised in the range of 0.80 to 1.00, and preferably in the range of 0.88 to 0.98. In the present invention, when the raw synthesis gas produced has a Z ratio very close to 1.00, the operating conditions and the process parameters of the primary and secondary reformers would be the same as described in British Pat. No. 1,569,014. However, when the raw synthesis gas produced in the present invention has a Z ratio lower than 1.00, then less reforming is performed in the primary steam reformer and more reforming is performed in the secondary oxygen reformer as compared to the process of British Pat. No. 1,569,014. To accomplish less reforming in the primary reformer requires changing the operating conditions in one of the two following ways:

either treat a smaller fraction of the total feedstock in primary steam reformer and keep the outlet temperature from the primary steam reformer at the same level as in the British patent, or treat the same fraction of the total feedstock in the primary steam reformer and reduce the outlet temperature from the reformer.

The raw synthesis gas thus produced is mixed with a hydrogen-rich stream obtained by subjecting the purge gas from the synthesis loop to a physical separation. This mixture is the final synthesis gas which is fed to the synthesis loop. The amount of hydrogen that is mixed with the raw synthesis gas is sufficient to provide a final synthesis gas having optimum desired Z ratio, which can be equal to or different from 1.00.

Figure 2:
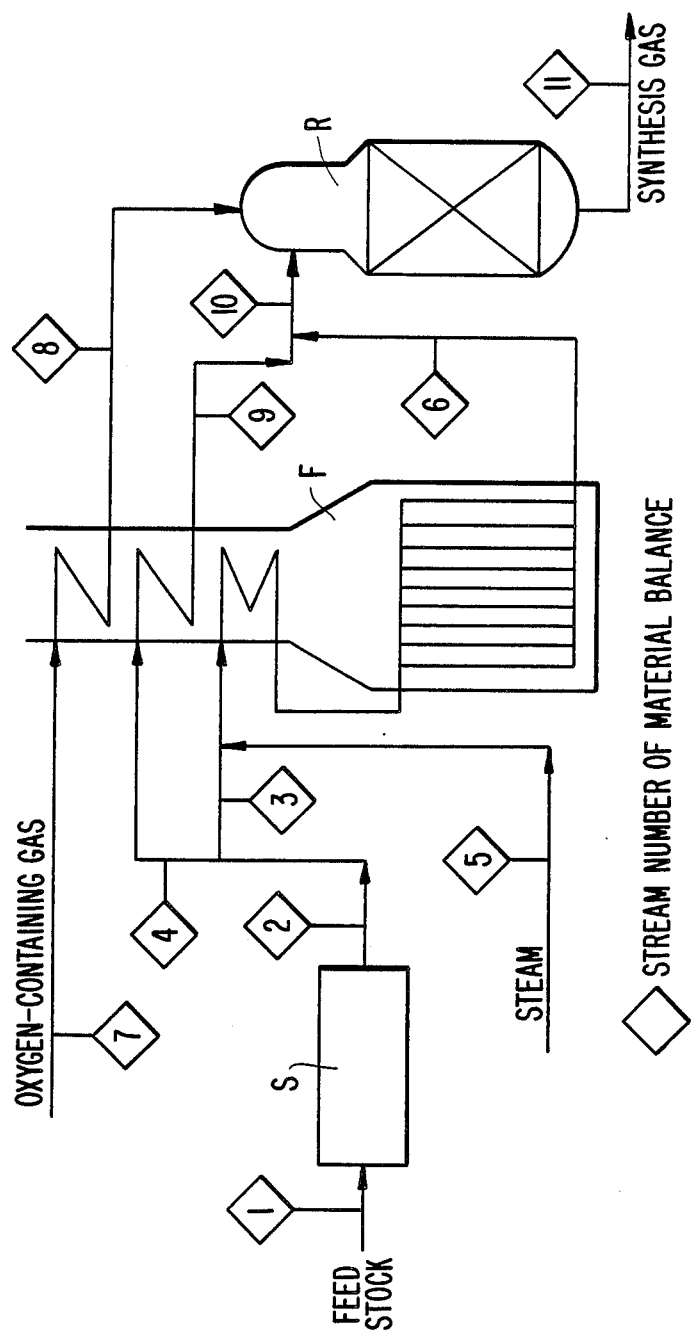
FIG. 2 is a schematic diagram showing the production of the raw synthesis gas in accordance with the present invention.

In accordance with the present invention and as shown in FIG. 2, a feedstock in stream 1 is introduced into a zone S wherein it is desulfurized by conventional techniques and apparatus. The pressure on the feedstock must be raised to the level required by the reforming process. This increase in pressure may be accomplished either before or after the desulfurization. After compression, the feedstock in stream 2 is divided into two fractions. The first fraction is mixed with steam from stream 5, and the mixture is injected into the reforming tubes of a reforming heater F at a temperature generally between about 300° to 600° C.

The amount of steam mixed with the first fraction is generally expressed by the ratio of the number of moles of $H_2O$ to the number of carbon atoms contained in the hydrocarbons in the feedstock. This ratio is commonly known as the steam/carbon ratio. Depending on the elemental composition of the feedstock and the application contemplated for the synthesis gas (and possibly the operating pressure, and/or the activity and selectivity of the catalysts used) it is possible to use, in the process of the present invention, a wide range of steam/carbon ratios, extending from 1.2 to 5.0.

The endothermic primary steam reforming reaction which takes place inside the reforming tubes, on contact with the catalyst, converts the feedstock and steam into a gas mixture containing hydrogen, carbon oxides, methane, and a small amount of ethane, with all the other hydrocarbons being completely converted. The heat required for said endothermic reaction is supplied by the burners of primary reforming heater F.

One of the main features in the process of the present invention is that the temperature of the process gas effluent from the primary steam reforming is very moderate, generally being between 650° and 850° C. and preferably between 720° and 780° C. Because the process operates at these moderate temperatures, it is possible to operate at a high pressure above 15 atm and pressures appreciably higher than 30 atm, for example between 50 and 120 atm. It can operate at this pressure using reforming tubes made of the same refractory alloys as presently used in commercial practice. As a consequence, the residual methane content in the gas effluent, in stream 6, from primary steam reforming heater F is comparatively high, that is above 10 per cent by volume on a dry basis.

The second fraction of the feedstock in stream 4 is preferably preheated to a temperature above 200° C., and is then mixed with the gas effluent, in stream 6, from the primary reformer F, to obtain the mixture in stream 10 which contains at least 35 percent of methane equivalent.

The mixture in stream 10 is injected into a single stage secondary oxygen reformer R wherein it is reacted with a free-oxygen rich gas (introduced into the reactor through stream 7) having a total amount of nitrogen and rare gases below 20 per cent by volume, and preferably below 5 per cent by volume. Accordingly, the free-oxygen rich gas has a molecular oxygen content of at least 80 per cent by volume on a dry basis. The oxygen stream, prior to injecting into the oxygen reformer, may be preheated to a temperature, for example, in the range of 200° to 500° C.

The secondary reformer R in the present invention is similar to those presently used industrially, it is essentially made of a refractory lined vessel and composed of a gas mixing zone, where the reacting gases are first contacted, and a reaction zone which contains a single catalyst bed, although the catalyst bed may contain two or more layers of different catalysts. If the temperature of the reacting streams 8 and 10 is above about 400° to 500° C., the partial oxidation reaction will be initiated in the gas mixing zone of reactor R at the point of contact between the oxygen stream 8 and the feed mixture stream 10.

The overall exothermic reaction which takes place adiabatically in secondary reformer R raises appreciably the temperature of the reacting gas mixture, to a level comprised between 850° and 1250° C., and preferably between 950° and 1100° C. The conditions of the reacting gases in the gas mixing zone of reactor R, in the present invention, are much more severe than those presently practiced in the synthesis gas industry. This is so because the oxygen concentration in the mixture is much higher then in conventional processes, because the feed to this reactor contains significantly higher hydrocarbon content, namely above 35 per cent methane equivalent, and also because of the fact that the mixture of stream 10 may contain hydrocarbons heavier than methane. As is known in the prior art, and mentioned above, there is a risk of carbon formation and excessive temperatures under such severe conditions.

In the concept underlying the present invention, such carbon formation, when it occurs, is tied to the kinetics of the reactions. More specifically, the oxygen reaction rate with hydrogen and hydrocarbons is very high compared to that at which the reacting gases are mixed together. Therefore, if the reaction is proceeding significantly while the mixture is still very heterogeneous, those fractions having a great excess of oxygen will reach very high temperatures. The oxygen deficient fractions will be subjected to thermal cracking, leading to carbon formation in the temperature range of about 400° to about 600° C. The heat needed to drive the thermal cracking reaction is transmitted by radiation from the reaction occurring in the oxygen-rich fraction. According to this concept, when the temperature of the incoming streams 8 and 10 is above about 400° C., such risks of carbon formation and excessive temperatures are obviated by injecting the reacting gases to the oxygen reformer R through a mixing apparatus designed to obtain quasi instantaneously a homogenous mixture before the partial oxidation reaction proceeds significantly. One such apparatus is disclosed in Canadian Pat. No. 1,116,856 and European Pat. No. 001946. However, other apparatus can be suitably employed.

The fraction of the feedstock to be treated in the primary steam reformer depends on several factors, as the feedstock composition, the desired ratio Z in the final synthesis gas, the outlet temperature form the primary reformer, the steam to carbon ratio in the latter. For a natural gas feedstock and a ratio Z in the final synthesis gas equal 1.00 or very close to that figure, the fraction of the feed in the primary reformer may vary from 5 to 60 percent of the total feedstock, and preferably from 15 to 40 percent of the total feedstock. When the desired ratio Z in the final synthesis gas is appreciably lower than 1.00, for example lower than 0.95, the first fraction in the primary reformer may be as low as 3 % of the total feedstock. It is of course realized that to produce a minimum amount of hydrogen which is needed in the secondary oxygen reformer to prevent carbon formation, it is possible either to treat in the primary reformer a small fraction of the total feeds, such as 3% to 25%, with a corresponding high outlet temperature from said reformer, such as 750° to 850° C., or to treat in the primary reformer a larger fraction of the total feed, such as 15 to 60 percent, with a corresponding lower outlet temperature, such as 680° to 770° C. Both ways are equally acceptable for reducing to practice the present invention. It is also realized that the minimum amount of hydrogen to be produced depends very much on the feedstock composition, and on the inlet temperatures of streams 8 and 10 to the secondary reformer. The minimum amount increases with the inlet temperatures, and with the molecular weight of the feedstock.

The oxygen is consumed entirely in the course of the reaction, and the synthesis gas thus produced in stream 11 contains a small amount of residual methane, less than five percent, and preferably less than three percent by volume on a dry basis, the lower methane content being desirable to limit the amount of purge gas from the synthesis loop. In any case, this residual methane percentage, or the percent methane equivalent, is less than one-seventh of the percent methane equivalent of the feed to the secondary reformer, and preferably less than one-tenth of the percent methane equivalent of said feed.

The Z ratio of the effluent in stream 11 from the secondary oxygen reformer R can vary in a wide range from 0.80 to 1.00. However, in applications where the desired Z ratio in the final synthesis gas is equal or close to 1.00, the Z ratio of the secondary reformer effluent is preferably between 0.90 and 0.98, and in many cases could advantageously be between 0.92 and 0.96.

The catalysts used in the primary steam reformer F and the secondary oxygen reformer R can be any ones of the conventional catalysts presently used in commercial practice for the production of synthesis gases from hydrocarbons. These conventional catalysts usually contain one or more of the following active components: nickel, nickel oxide, cobalt oxide, chromia and molybdenum oxide. The active component may be supported on a refractory support such as aluminum oxide, an alkaline earth oxide, zirconium oxide, or a combination thereof. A promoter can be included in the catalyst, including thorium, cerium, cesium, an alkaline oxide, or combination thereof. The composition and method of preparation of the catalysts form no part of this invention. However, the following U.S. patents disclose more information on catalysts useful in the invention: 3,264,066, 3,442,613, 3,763,205, and 4,079,017. "Catalyst Handbook" 1970, Wolfe Scientific Books, London, Chapter 5, pages 64–96 and "Steam Reforming Catalysts" by J. R. Rostrup-Nielsen, 1975, Teknisk Forlag A/S, Copenhagen, Chapter 2, pages 38–48, disclose further information on the conventional catalysts useful in the invention.

In accordance with the claimed invention and as shown in FIG. 1, the gas effluent in steam 11 from the secondary reformer R is then mixed with at least part of the hydrogen rich stream obtained by physical separation of the purge gas from the synthesis loop. The resulting mixture comprises the final synthesis gas and has the desired Z ratio for injecting into the synthesis loop. This ratio can be either close or equal to 1.00, or appreciably lower or higher than 1.00.

Figure 3:
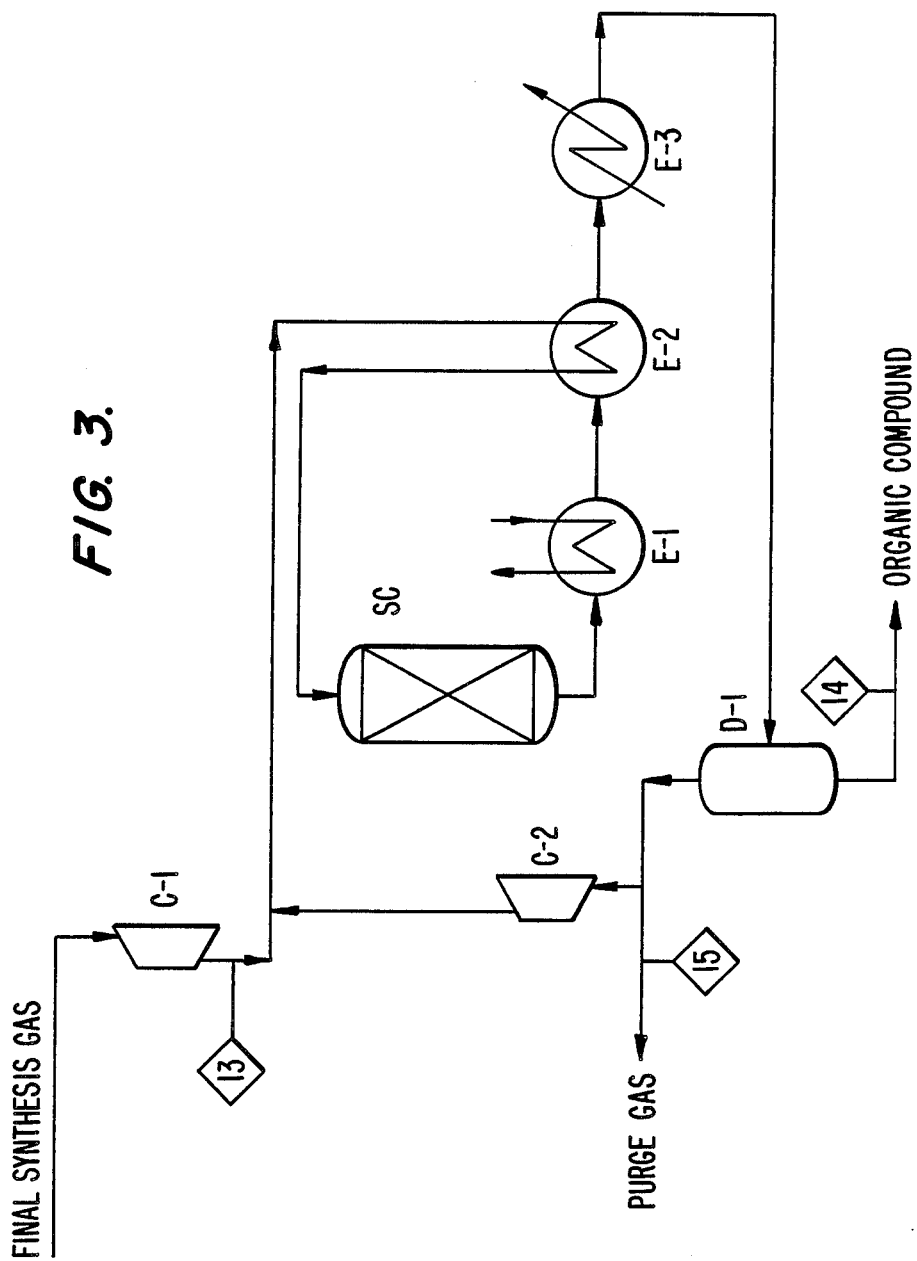
FIG. 3 is a schematic diagram showing a synthesis loop for the production of methanol, higher alcohols, or other organic compounds.

The final synthesis gas is next injected into the synthesis loop, as shown in FIG. 3, wherein it is converted to methanol or the desired organic compound. Since the final synthesis gas is usually produced at a lower pressure than that required for the synthesis reaction, it is first compressed in compressor C-1 and then mixed with the recycle gas coming from the discharge of compressor C-2. The mixture is then preheated in heat exchanger E-2 and then injected into the synthesis converter SC which contains an appropriate catalyst for the desired organic product. This synthesis converter SC operates either adiabatically, with a corresponding outlet temperature higher than the inlet temperature, or essentially isothermally if the heat of reaction is transferred simultaneously for steam generation. The gas effluent from SC is first cooled in heat exchanger E-1, which can be a waste heat boiler for example, then in heat exchanger E-2 for preheating the feed to synthesis converter SC, and then in water cooler E-3 where most of the organic product is condensed together with the water produced in the reaction. The liquid is then separated from the gas in separator D-1. A small fraction of the gas leaving separator D-1 is extracted from the loop as purge gas, in order to maintain at a reasonable level the concentration of inert gases in the loop. The remainder of the gas is compressed in recycle compressor C-2 and mixed with the compressed final synthesis gas, thereby closing the loop as mentioned above. The duty of compressor C-2 is merely to compensate the pressure drop in the loop. The pressure and temperature in the synthesis converter SC may vary over a wide range, as reported in the above cited literature on the production of organic compounds from synthesis gas.

The purge gas (stream 15) extracted from the synthesis loop is subjected to a physical separation to split it into a hydrogen-rich stream, a portion of which will be mixed with the raw synthesis gas to form the final synthesis gas, and a residual gas stream which contains essentially methane, carbon oxides, argon, nitrogen, and some hydrogen, and which can be used as fuel in the primary stream reformer.

Any physical separation process can be used. One typical physical separation process for this purpose is the well known Pressure Swing Absorption (PSA) process, which is described in U.S. Pat. Nos. 3,986,849, 4,333,744, 4,381,189, 4,461,630, and 4,475,929, and in Hydrocarbon Processing, January 1978, pages 175–177 and March 1979, pages 119–122. The physical separation can also be achieved by cryogenic techniques, or distillation at low temperature, such as outlined in Chemical Engineering Progress, February 1980, pages 72–79 and Oct. 1984, pages 53–56. Another physical separation for this purpose is the membrane separation process, which is described in Hydrocarbon Processing May 1980 pages 115–118, and July 1980 pages 65–67.

Figure 4:
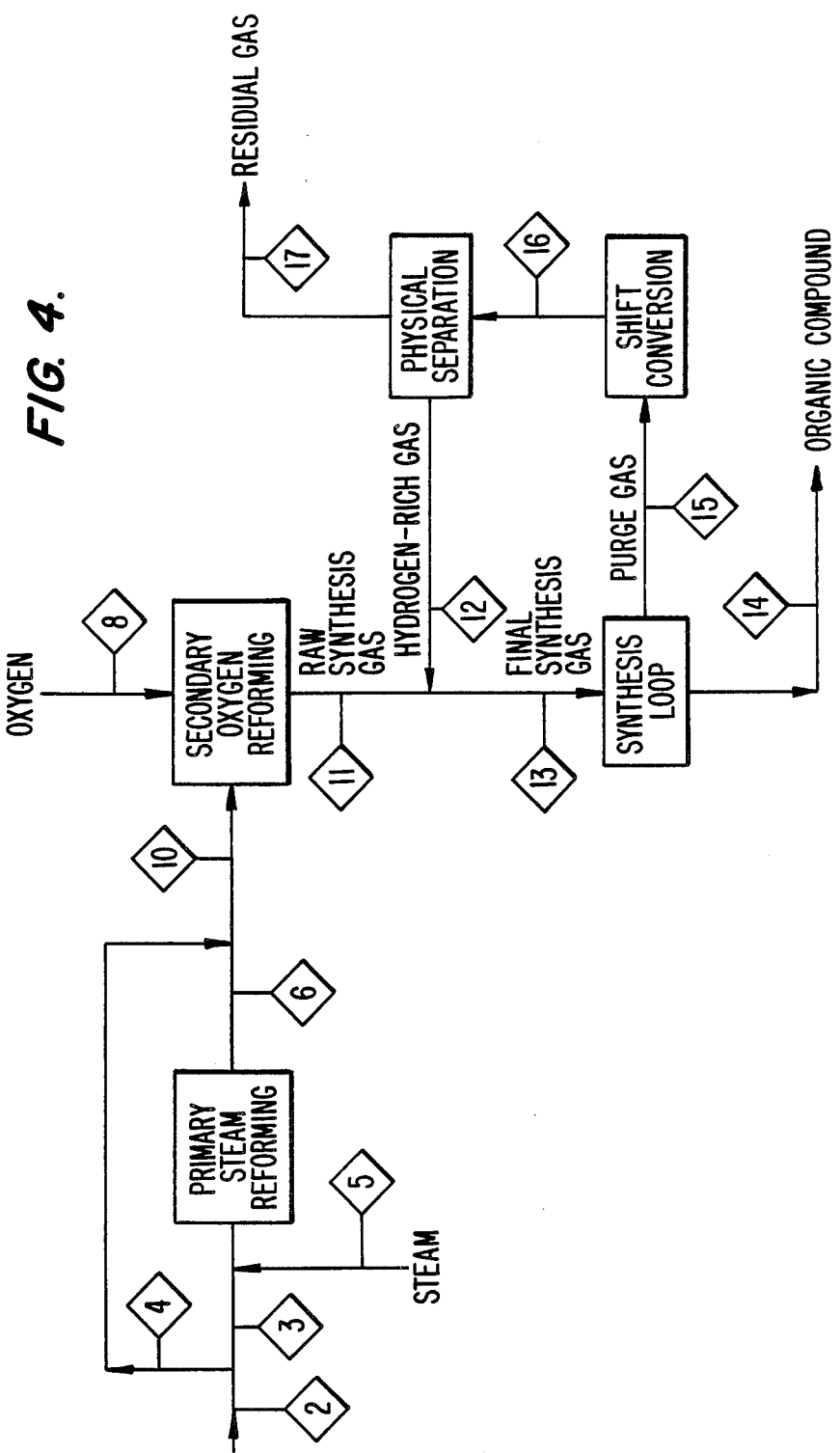
FIG. 4 is a block flow diagram showing a second embodiment of the invention wherein the purge gas is subjected to a shift conversion prior to physical separation.

FIG. 4 represents another embodiment of the present invention, in which the purge gas from the synthesis loop is first subjected to a shift conversion reaction and then to physical separation. In the shift conversion reaction, essentially all the carbon monoxide in the purge gas reacts with steam, in the presence of a shift conversion catalyst, to form carbon dioxide and hydrogen. The shift catalyst that is preferred in this process may be either a "high temperature shift" (HTS) catalyst, based on iron and chromium oxides, or a "low temperature shift" (LTS) catalyst which is based on copper and zinc oxides, or any combination thereof. An HTS catalyst operates usually at a temperature between 380° C. and 480° C., whereas the LTS catalyst operates at a temperature between 180° C. and 260° C.

Shift conversion increases the amount of hydrogen that can be recovered from the purge gas in the physical separation. This would be desirable or necessary when the difference between the Z ratios of the raw and final synthesis gases requires more hydrogen then is contained in the hydrogen-rich steam that would be obtained without shift conversion.

Figure 5:
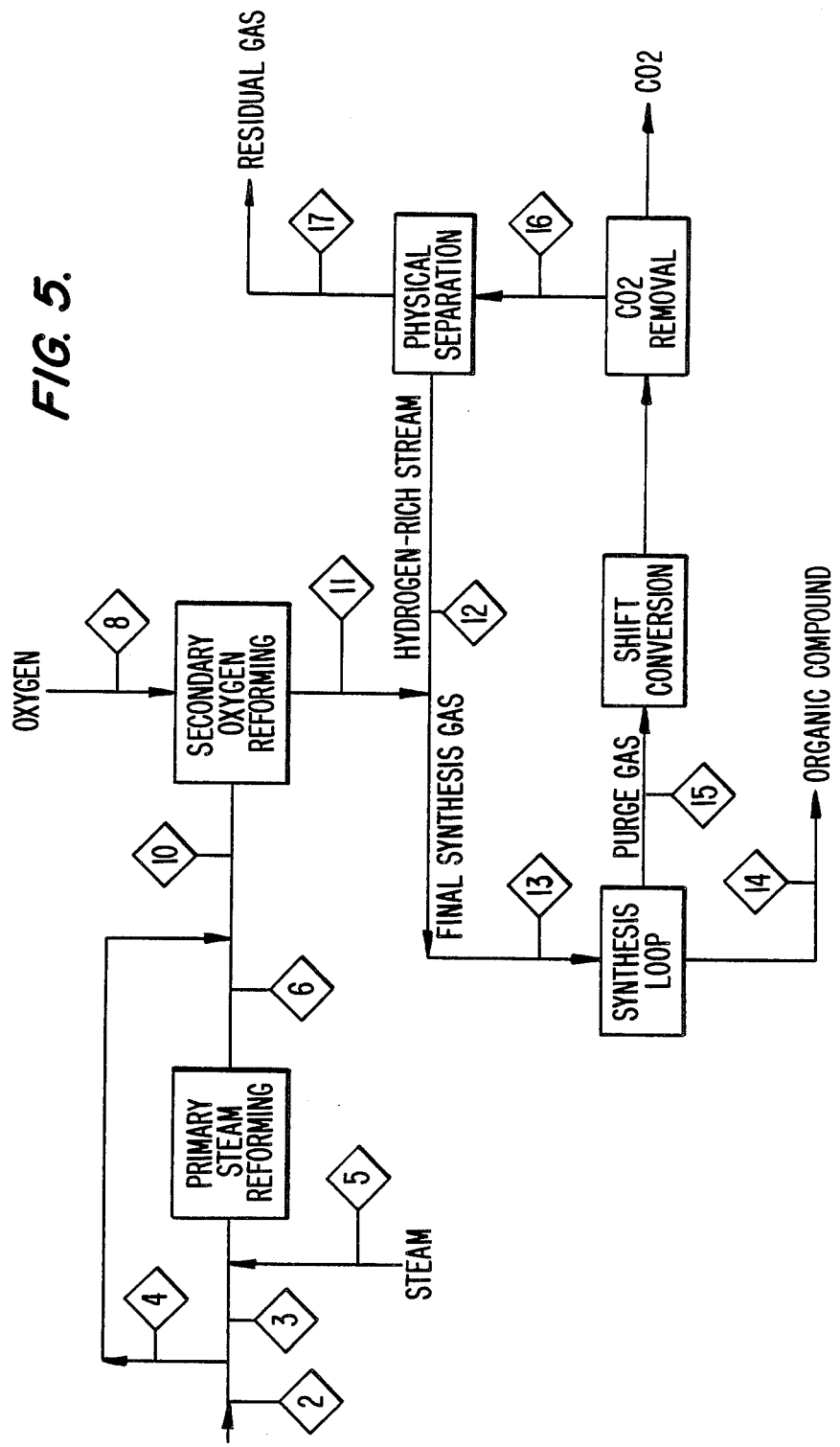
FIG. 5 is a block flow diagram showing a third embodiment of the invention wherein $CO_2$ is removed from the purge gas after the shift conversion step.

When the purge gas is subjected to a shift conversion reaction, another ebodiment of the present invention involves performing the physical separation downstream in two steps, as shown on FIG. 5. In the first step, essentially all the $CO_2$ is removed by scrubbing the gas in a tower with an appropriate solution such as amines or potassium carbonate. The solvent is then regenerated in a second tower. The towers may be equipped with gas-liquid contact devices such as trays or packings. Any known process for $CO_2$ removal is acceptable in the process of the invention. In the second step, any one of the above mentioned physical separation processes may be used to separate a hydrogenrich stream from a residual gas containing essentially methane, some carbon monoxide, and hydrogen.

The present invention is also used with more than one feedstock. In such a case, the feedstocks can be mixed at the start, partially or completely, and then proceed with the split between the first and second fractions as described above. Alternatively, one or two of the feedstocks can be steam reformed in the primary steam reforming and the other feedstocks could be injected directly into the secondary oxygen reformer. These various means of combining the feedstocks, although not represented in the aforesaid examples are within the spirit of the present invention, which is based on an original combination of processing steps, the combination offering the same advantages whatever number and combination of feedstocks are used.

EXAMPLES

Table I shows an example of anticipated temperatures, gas pressures, flow rates and compositions at significant positions in a process according to FIGS. 2-3-4, for the production of 2499.8 metric tons/day of methanol. In this example, 20% (stream 3) of the total natural gas feedstock is treated in the primary steam reformer, and 80% (stream 4) of the feedstock is mixed with the effluent from the primary steam reformer. The effluent from the secondary reformer (raw synthesis gas) has a Z ratio of 0.954. The purge gas (stream 15) is first subjected to a shift conversion reaction, thereby reducing its CO content to about 2.2% on a dry basis, and then separated in a PSA system producing the hydrogen rich-stream 12 which is mixed with the raw synthesis gas, thereby increasing the Z ratio from 0.954 to 1.000 at the inlet of the synthesis loop. The methanol synthesis operates at a pressure of about 78 bar g, over a copper based catalyst which is widely used commercially. The hydrogen yield in the PSA system amounts to about 90%.

Table II shows another example of anticipated temperatures, gas pressures, flow rates and compositions at significant positions in a process according to FIGS. 2-3-5, for the production of 2499.8 metric tons/day of methanol. In this example, 10% (stream 3) of the total natural gas feedstock is treated in the primary steam reformer, and 90% (stream 4) of the feedstock is mixed with the effluent from the primary steam reformer. The effluent from the secondary reformer (raw synthesis gas) has a Z ratio of 0.9325. The purge gas (stream 15) is first subjected to a shift conversion reaction, thereby reducing its CO contant to about 0.7% on a dry basis. It is then subjected to $CO_2$ removal by scrubbing against a monoethanolamine solution after which it is subjected to a cryogenic separation producing the hydrogen-rich stream (stream 12) which is mixed with the raw synthesis gas, thereby increasing the Z ratio from 0.9325 to 0.9861 at the inlet of the synthesis loop. The methanol synthesis operates at a pressure of about 78 bars g, over a copper based catalyst which is widely used commercially. The hydrogen yield in the cryogenic separation amounts to about 96%.

TABLE I

| STREAM NUMBER | 2 | 3 | 4 | 5 | 6 | 7 | 8 | 9 |
|---|---|---|---|---|---|---|---|---|
| $H_2$ kg. mol/hr | — | — | — | — | 1167.3 | — | — | — |
| CO kg. mol/hr | — | — | — | — | 135.7 | — | — | — |
| $CO_2$ kg. mol/hr | — | — | — | — | 194.0 | — | — | — |
| $CH_4$ kg. mol/hr | 3530.3 | 706.0 | 2824.3 | — | 406.5 | — | — | 2824.3 |
| Ar kg. mol/hr | — | — | — | — | — | 9.2 | 9.2 | — |
| $O_2$ kg. mol/hr | — | — | — | — | — | 1835.4 | 1835.4 | — |
| $H_2O$ kg. mol/hr | — | — | — | 1987.6 | 1463.9 | 96.6 | 96.6 | — |
| $CH_3OH$ kg. mol/hr | — | — | — | — | — | — | — | — |
| i-butyl alcohol kg. mol/hr | — | — | — | — | — | — | — | — |
| di-methyl ether kg. mol/hr | — | — | — | — | — | — | — | 51.9 |
| $C_2H_6$ | 64.9 | 13.0 | 51.9 | — | — | — | — | 5.7 |
| $C_3H_8$ kg. mol/hr | 7.1 | 1.4 | 5.7 | — | — | — | — | 2881.9 |
| Total kg. mol/hr | 3602.3 | 720.4 | 2881.9 | 1987.6 | 3367.4 | 1941.2 | 1941.2 | 371 |
| Temperature °C. | 30 | 30 | 30 | 371 | 769 | 120 | 550 | 38.9 |
| Pressure Bar G | 43 | 43 | 43 | 43 | 38.9 | 40.6 | 39.5 | — |
| STREAM NUMBER | 10 | 11 | 12 | 13 | 14 | 15 | 16 | 17 |
| $H_2$ kg. mol/hr | 1167.3 | 6916.2 | 333.5 | 7249.7 | 21.7 | 331.1 | 370.6 | 37.1 |
| CO kg. mol/hr | 135.7 | 2999.5 | — | 2999.5 | 4.7 | 54.8 | 15.3 | 15.3 |
| $CO_2$ kg. mol/hr | 194.0 | 416.9 | — | 416.9 | 41.7 | 36.2 | 75.7 | 75.7 |
| $CH_4$ kg. mol/hr | 3230.8 | 265.0 | — | 265.0 | 44.5 | 220.4 | 220.4 | 220.4 |
| Ar kg. mol/hr | — | 9.2 | 0.2 | 9.4 | 0.9 | 8.5 | 8.5 | 8.3 |
| $O_2$ kg. mol/hr | — | — | — | — | — | — | — | — |
| $H_2O$ kg. mol/hr | 1463.9 | 1921.7 | — | 9.0 | 365.1 | 0.1 | 1.1 | 1.1 |
| $CH_3OH$ kg. mol/hr | — | — | — | — | 3250.7 | 2.4 | 2.4 | 2.4 |
| i-butyl alcohol kg. mol/hr | — | — | — | — | 4.3 | — | — | — |
| di-methyl ether kg. mol/hr | — | — | — | — | 4.2 | 0.2 | 0.2 | 0.2 |
| $C_2H_6$ | 51.9 | — | — | — | — | — | — | — |
| $C_3H_8$ kg. mol/hr | 5.7 | — | — | — | — | — | — | — |
| Total kg. mol/hr | 6249.3 | 12528.5 | 333.7 | 10949.5 | 3737.8 | 653.7 | 694.2 | 360.5 |
| Temperature °C. | 540 | 1062 | 35 | 35 | 35 | 35 | 35 | 35.0 |
| Pressure Bar G | 38.9 | 38.3 | 36.0 | 84.0 | 77.2 | 77.2 | 38.0 | 0.3 |
| | — | 0.954 | — | 1.0 | — | — | — | — |

TABLE II

| STREAM NUMBER | 2 | 3 | 4 | 5 | 6 | 7 | 8 | 9 |
|---|---|---|---|---|---|---|---|---|
| $H_2$ kg. mol/hr | — | — | — | — | 698.3 | — | — | — |
| CO kg. mol/hr | — | — | — | — | 99.2 | — | — | — |
| $CO_2$ kg. mol/hr | — | — | — | — | 102.2 | — | — | 3273.6 |
| $CH_4$ kg. mol/hr | 3637.4 | 363.8 | 3273.6 | — | 177.9 | — | — | — |
| Ar kg. mol/hr | — | — | — | — | — | 9.5 | 9.5 | — |
| $O_2$ kg. mol/hr | — | — | — | — | — | 1930.4 | 1930.4 | — |
| $H_2O$ kg. mol/hr | — | — | — | 1024.2 | 720.6 | 101.9 | 101.9 | — |
| $CH_3OH$ kg. mol/hr | — | — | — | — | — | — | — | — |
| i-butyl alcohol kg. mol/hr | — | — | — | — | — | — | — | — |
| di-methyl ether kg. mol/hr | — | — | — | — | — | — | — | 60.1 |
| $C_2H_6$ | 66.8 | 6.7 | 60.1 | — | — | — | — | 6.9 |
| $C_3H_8$ kg. mol/hr | 7.6 | 0.7 | 6.9 | — | — | — | — | 3340.6 |
| Total kg. mol/hr | 3711.8 | 371.2 | 3340.6 | 1024.2 | 1798.2 | 2041.8 | 2041.8 | 371 |
| Temperature °C. | 30 | 30 | 30 | 371 | 807 | 120 | 550 | 38.9 |
| Pressure Bar G | 43 | 43 | 43 | 43 | 38.9 | 40.6 | 39.5 | — |
| STREAM NUMBER | 10 | 11 | 12 | 13 | 14 | 15 | 16 | 17 |
| $H_2$ kg. mol/hr | 698.3 | 6712.1 | 386.1 | 7098.2 | 17.8 | 320.9 | 402.2 | 16.1 |
| CO kg. mol/hr | 99.2 | 3173.1 | — | 3173.1 | 6.4 | 87.1 | 5.8 | 5.8 |

TABLE II-continued

| | | | | | | | | |
|---|---|---|---|---|---|---|---|---|
| CO₂ kg. mol/hr | 102.2 | 283.9 | — | 283.9 | 42.0 | 41.9 | — | — |
| CH₄ kg. mol/hr | 3451.5 | 336.8 | — | 336.8 | 49.8 | 287.3 | 287.3 | 287.3 |
| AR kg. mol/hr | — | 9.5 | 0.8 | 10.3 | 0.9 | 9.4 | 9.4 | 8.6 |
| O₂ kg. mol/hr | — | — | — | — | — | — | — | — |
| H₂O kg. mol/hr | 720.6 | 1246.0 | — | 8.8 | 226.2 | 0.1 | 1.1 | 1.1 |
| CH₃OH kg. mol/hr | — | — | — | — | 3250.7 | 2.8 | 2.8 | 2.8 |
| i-butyl alcohol kg. mol/hr | — | — | — | — | 4.3 | — | — | — |
| di-methyl ether kg. mol/hr | — | — | — | — | 4.1 | 0.2 | 0.2 | 0.2 |
| C₂H₆ kg. mol/hr | 60.1 | — | — | — | — | — | — | — |
| C₃H₈ kg. mol/hr | 6.9 | — | — | — | — | — | — | — |
| Total kg. mol/hr | 5138.8 | 11761.4 | 386.9 | 10911.1 | 3602.2 | 749.7 | 708.8 | 321.9 |
| Temperature °C. | 480 | 1080 | 35 | 35 | 35 | 35 | 35 | 35 |
| Pressure Bar G | 38.9 | 38.3 | 36.0 | 84.0 | 77.2 | 77.2 | 38 | 0.3 |
| | — | 0.9325 | — | 0.9861 | — | — | — | — |

While particular embodiments of the present invention have been described, it will be understood, of course, that this invention is not limited thereto since many modifications may be made, and it is therefore contemplated to cover by the appended claims any and all such modifications as may fall within the true spirit and scope of this invention.

What is claimed is:

1. A process for producing an oxygenated hydrocarbon or mixtures thereof from a hydrocarbon containing feedstock, which comprises:
   (a) dividing said feedstock into two fractions,
   (b) subjecting the first fraction from (a) to a primary steam reforming reaction, by mixing said fraction with steam and heating the mixture thereof by indirect heat exchange, in the presence of a reforming catalyst, to form a gaseous effluent including hydrogen at a temperature between 650° and 850° C.,
   (c) mixing the gas effluent from (b) with the second fraction from (a),
   (d) reacting in a single stage the gas mixture from (c) with a free oxygen-rich gas, in a secondary reforming reactor operating under essentially adiabatic conditions, and containing a single bed of catalyst, thus producing a synthesis gas at a temperature between 850° and 1250° C., containing a percent methane equivalent of less than one-tenth of that of the gas mixture from (c), and having a Z ratio of between 0.80 and 1.00, where Z is defined as:

$$Z = \text{moles } H_2 \, [2(\text{moles CO}) + 3(\text{moles CO}_2)]$$

(e) mixing the gas effluent from (d) with a hydrogen-rich stream free from carbon oxides to form a final synthesis gas stream,
   (f) injecting said final synthesis gas into a synthesis loop, forming said oxygenated hydrocarbon or mixtures thereof in said loop, and extracting from said loop a purge gas stream,
   (g) separating said purge gas stream in a physical separation to form a hydrogen-rich gas stream free from carbon oxides and a residual gas stream, and
   (h) recycling at least a portion of said hydrogen-rich gas stream to step (e).

2. The process of claim 1 wherein said purge gas stream is first subjected to a shift conversion reaction, by reacting said purge gas with steam in the presence of a shaft catalyst, and then to said physical separation.

3. The process of claim 1 wherein said purge gas stream is subjected to a shift conversion reaction, by reacting said purge gas with steam in the presence of a shift catalyst, and then to the removal of carbon dioxide from said shift converted gas, and then to said physical separation.

4. The process of claims 1, 2, or 3, wherein the gas effluent temperature from said steam reforming reaction in step (b) is between about 720° and about 780° C.

5. The process of claims 1, 2, or 3, wherein the gas effluent temperature from said secondary oxygen reforming reactor is between about 950° and about 1100° C.

6. The process of claims 1, 2, or 3 wherein the gas effluent from said secondary oxygen reforming reactor has a z ratio of between 0.88 and 0.98.

7. The process of claims 1, 2, or 3 wherein the gas mixture from (e) has a z ratio essentially equal to 1.00.

8. The process of claims 1, 2, or 3 wherein said free oxygen-rich gas has a molecular oxygen content of at least 80% by volume.

9. The process of claims 1, 2, or 3 wherein said free-oxygen-rich gas has a molecular oxygen content of at least 95% by volume.

10. The process of claims 1, 2, or 3 wherein said first fraction of the feedstock treated in the primary steam reforming reactor is between about 5 and about 60% of the total feedstock.

11. The process of claim 10 wherein said first fraction of the feedstock treated in the primary steam reforming reactor is between 10% and 30% of the total feedstock.

12. The process of claims 1, 2, or 3 wherein the pressure in the primary steam reforming reactor and the secondary oxygen reforming reactor is above 30 bars.

13. The process of claims 1, 2, or 3 wherein said physical separation in step (g) is achieved by selective absorption over molecular sieves.

14. The process of claims 1, 2, or 3 wherein said physical separation in step (g) is achieved by selective diffusion though a membrane.

15. The process of claims 1, 2, or 3 wherein said physical separation in step (g) is achieved by distillation at low temperature.

* * * * *

UNITED STATES PATENT AND TRADEMARK OFFICE
CERTIFICATE OF CORRECTION

PATENT NO. : 4,782,096

DATED : November 1, 1989

INVENTOR(S) : David BANQUY

It is certified that error appears in the above-identified patent and that said Letters Patent is hereby corrected as shown below:

On the front page, there should be inserted the following:

-- Related U.S. Application Data
   [63] Continuation of Serial No. 827,558,
   filed Feb. 10, 1986, Abandoned.--

Signed and Sealed this

Twenty-fifth Day of September, 1990

Attest:

HARRY F. MANBECK, JR.

*Attesting Officer*　　　　*Commissioner of Patents and Trademarks*